United States Patent [19]

Yamagiwa et al.

[11] 4,421,738

[45] Dec. 20, 1983

[54] SUGAR-COATED TABLET CONTAINING FAT-SOLUBLE PHARMACEUTICAL MATERIAL

[75] Inventors: Satoshi Yamagiwa, Isezaki, Japan; Yoshio Taguchi, Takao, China; Masanori Kayano, Honjo, Japan

[73] Assignee: Eisai Co., Ltd., Tokyo, Japan

[21] Appl. No.: 359,407

[22] Filed: Mar. 18, 1982

Related U.S. Application Data

[63] Continuation of Ser. No. 169,325, Jul. 16, 1980, abandoned.

[30] Foreign Application Priority Data

Jul. 31, 1979 [JP] Japan ................................ 54-96677

[51] Int. Cl.³ .............................................. A61K 9/36
[52] U.S. Cl. ........................................ 424/35; 424/16; 424/21
[58] Field of Search ...................................... 424/35, 16

[56] References Cited

U.S. PATENT DOCUMENTS

| | | | |
|---|---|---|---|
| 2,693,436 | 11/1954 | Spradling | 424/35 |
| 2,816,062 | 12/1957 | Doerr et al. | 424/35 |
| 2,881,085 | 4/1959 | Endiott et al. | 424/32 |
| 2,925,365 | 2/1960 | Nicholson et al. | 424/35 |
| 3,043,747 | 7/1962 | Long | 424/35 |
| 3,054,724 | 9/1962 | Raff | 424/35 |
| 3,096,248 | 7/1963 | Rudzki | 424/35 |
| 3,185,626 | 5/1965 | Baker | 424/35 |
| 3,256,111 | 6/1966 | Singiser | 424/35 |
| 3,361,631 | 1/1968 | Weinstein | 424/35 |
| 3,371,015 | 2/1968 | Sjogren et al. | 424/35 |
| 3,383,236 | 5/1968 | Brindamour | 424/35 |
| 3,406,031 | 10/1968 | Lee | 424/35 |
| 3,480,468 | 11/1969 | Carletti et al. | 424/35 |
| 3,981,984 | 9/1976 | Signorino | 424/35 |
| 4,001,390 | 1/1977 | Ohno et al. | 424/35 |
| 4,176,175 | 11/1979 | Maekawa et al. | 424/35 |

*Primary Examiner*—Shep K. Rose
*Attorney, Agent, or Firm*—Flynn, Thiel, Boutell & Tanis

[57] ABSTRACT

A sugar-coated tablet for medical use comprising a core containing low-melting fat-soluble pharmaceutical material and a sugar coating layer on said core, which is characterized by the feature that at least one water-soluble cellulose ether coating film is present between the core and the sugar-coating layer.

8 Claims, No Drawings

SUGAR-COATED TABLET CONTAINING FAT-SOLUBLE PHARMACEUTICAL MATERIAL

This is a continuation, of application Ser. No. 169,325, filed July 16, 1980, now abandoned.

This invention relates to a sugar-coated tablet for medical use comprising, as a core, a base tablet containing low-melting fat-soluble active pharmaceutical material, and having a sugar coating layer on the base tablet, which is characterized by the feature that at least one water-soluble cellulose ether coating film is present between the base tablet and the sugar coating layer.

Sugar-coated tablets can be easily ingested by human beings and, therefore, they are often employed by pharmaceutical suppliers for facilitating the administration procedure. However, some inherent problems are present in the art of sugar-coated tablets which have been conventionally employed, and these problems have not been sufficiently solved until now. For this reason, there are certain limitations on the kinds of pharmaceuticals that can be included in sugar-coated tablets, even though sugar-coated tablets are of value as pharmaceutical unit dosage forms.

For example, it is preferred to prepare a low-melting fat-soluble pharmaceutical material in the form of a sugar-coated tablet for facilitating the administration, if such a unit dosage form can be employed. However, this preferred unit dosage form could not always be used up to now, because the technically difficult problems set forth below have not been solved, prior to the present invention.

According to the conventional art, a low-melting fat-soluble pharmaceutical material is initially adsorbed by a powdery substance whereby to make a powder pharmaceutical composition and then the powder pharmaceutical composition is prepared in the form of a tablet by adding an excipient and other auxiliary tablet-forming substances. If a sugar layer is coated directly on the thus-prepared tablet core, the preservability of the tablet is extremely deteriorated and, moreover, the solubility of the sugar coating layer at the time of administration of the sugar-coated tablet is also lowered. The cause of this is that when the thus-prepared sugar-coated tablet is stored at an elevated temperature, the low-melting fat-soluble pharmaceutical adsorbed by the powder is caused to melt whereby to acquire sufficient fluidity that the pharmaceutical easily exudes from the tablet core and permeates into the sugar coating layer. This means that when the sugar-coated tablet, prepared as described above, is subjected to storage at an elevated temperature, a large amount of the fat-soluble pharmaceutical becomes present in the sugar coating layer. These phenomena cause mainly the following two disadvantageous results.

The first disadvantageous result is that the fat-soluble pharmaceutical that has transferred into the sugar coating layer can be exposed to the ambient air to a greater degree than is the case when the pharmaceutical is entirely contained in the core of the tablet, so that the pharmaceutical is likely to be oxidized and decomposed whereby to change its color. The appearance of the surface of the sugar-coated tablet frequently changes during storage whereby to show red-brown dots or uneven coloring.

The second disadvantageous result is that the surface of the sugar-coated tablet becomes extremely hydrophobic due to the fat-soluble pharmaceutical that has transferred into the sugar coating layer, so that dissolving of the sugar coating layer, which is expected and intended to dissolve easily upon administration, is delayed, thereby causing the sugar coating layer to remain undissolved for a long time. Also, the thus-lowered solubility causes the sugar coated pharmaceutical tablet to fail the disintegration test. Further, the sugar-coated tablet having the lowered solubility is apt to pass through the human body without imparting the intended pharmaceutical action to the human body.

The present inventors have carried out a variety of studies for the purpose of solving the problems hereinbefore described and have discovered that these problems can be solved by placing a water-soluble cellulose ether film in a sugar-coated tablet between the core containing the low-melting fat-soluble pharmaceutical material and the sugar coating layer. The present invention has been completed based on this discovery.

In the specification, the term, base tablet, is called as usual uncoated tablet.

Accordingly, the present invention provides a sugar-coated tablet comprising, as a core, a base tablet containing one or more low-melting fat-soluble pharmaceutical substances, and a sugar coating layer covering said base tablet, in which at least one water-soluble cellulose ether coating film is present between the core tablet and the sugar coating layer. The object of the provision of this intermediate cellulose ether film is to keep fluidized, low-melting, fat-soluble pharmaceutical substances from transferring from the core tablet into the sugar coating layer.

The low-melting fat-soluble pharmaceutical substance employed in the present invention, is one that melts at a temperature of not higher than 70° C. Examples of such pharmaceuticals include Coenzyme Q, Vitamin K and its derivatives, Vitamin E and its derivatives, etc.

Examples of water-soluble cellulose ethers employed in the present invention include methyl cellulose, hydroxypropyl cellulose, hydroxyethyl cellulose, hydroxypropyl methyl cellulose and hydroxyethyl methyl cellulose. A film of one of these cellulose ethers exhibits a satisfactory effect on the prevention (permeation resistance) of the transfer of the low-melting, fat-soluble, pharmaceutical into the sugar coating layer.

A mixture of two or more of these water-soluble cellulose ethers can be employed, in combination, to prepare a film. The film prepared from such a combination provides a prevention effect similar to the effect provided by a film prepared from a single water-soluble cellulose ether.

The film of water-soluble cellulose ether can optionally contain a plasticizer, such as propylene glycol or polyethylene glycol, and the thus-contained plasticizer improves the characteristics of the film.

The film of water-soluble cellulose ether should have a thickness of at least 0.02 mm for providing the permeation prevention effect desired in the present invention. For most practical purposes, the thickness of the film ranges from 0.05 to 0.2 mm. For instance, the weight of the water-soluble cellulose ether film can be in the range of from 5 to 20 mg if a film consisting of hydroxypropyl cellulose and polyethylene glycol (3:1, by weight) is used to coat a base tablet weighing 90 mg (diameter 6.5 mm, thickness 3.25 mm).

Examples of solvents for dissolving or suspending the aforementioned water-soluble cellulose ethers and plasticizers include water, ethanol and a mixture of water and ethanol. However, there is no specific limitation on the solvent, and any effective inert organic solvent, compatible mixtures of such organic solvents or mixtures of water and an organic solvent can be employed, in addition to the water, ethanol and the mixture thereof mentioned previously.

There is no specific limitation on the procedure for coating the water-soluble cellulose ether film on the base tablet, so long as the procedure adopted can achieve the desired object. For instance, the film material solution or the film material suspension can be sprayed on the base tablets, while the base tablets are rolling in a rolling pan or are fluidized in a fluidized bed, in accordance with conventional tablet coating procedures.

The sugar coating can be carried out after completion of the coating of the water-soluble cellulose ether film, and the sugar coating procedure can be carried out in a conventional manner. For instance, a tablet coated with the cellulose ether film is dried by allowing it to stand overnight, then it is coated with powder sugar, then it is coated with a syrup (color coating) and finally it is coated with carnauba wax for glazing.

The effects of preventing the browning of the tablet surface and of preventing delayed disintegration thereof, which effects are otherwise caused by the permeation of the low-melting fat-soluble pharmaceutical into the sugar coating, which prevention is provided by the present invention, were determined by the tests set forth below.

(1) Prevention of browning disintegration
Samples: Sugar-coated tablets prepared in Examples 1-3, as set forth hereinafter, which employ hydroxypropyl cellulose (HPC) as the material of the water-soluble cellulose ether film, and sugar-coated tablets prepared in the same manner as described in Example 1, except that a cellulose ether film is not provided between the base tablet and the sugar coating layer (control sample).
Test procedure: One-hundred tablets are employed for each of the samples and are subjected to a temperature of 55° C. The number of tablets that undergo browning with the passing of time is counted.
Results: As shown in Table 1.

The effect of prevention of browning was further examined by employing, as an intermediate film between the core and the sugar coating, a film made of a copolymer of 2-methyl-5-vinylpyridine—methyl acrylate—methacrylic acid (trade name: MPM-47). Tablets prepared with that coating film were compared with tablets prepared using the water-soluble cellulose ether film of the present invention.
Samples: Sugar-coated tablets were prepared in the same manner as described in Examples 1 and 3, except that the MPM-47 material was employed as a material for forming the intermediate coating film, in place of the water-soluble cellulose ether coating film of the present invention.
Results: As shown in Table 2.

TABLE 1

| | Evaluation of HPC employed as intermediate film Number of Tablets That Showed Visible Browning | | | | | | |
|---|---|---|---|---|---|---|---|
| | Days | | | | | | |
| Sample | 1 | 7 | 14 | 21 | 30 | 45 | 60 |
| Product of Example 1 | 0 | 0 | 0 | 0 | 2 | 4 | 5 |
| Product of Example 2 | 0 | 0 | 0 | 0 | 0 | 0 | 0 |
| Product of Example 3 | 0 | 0 | 0 | 0 | 0 | 0 | 0 |
| Control Sample | 60 | 100 | 100 | 100 | 100 | 100 | 100 |

The weights of the films that were coated on the base tablets (each base tablet weighed 90 mg) were 5 mg, 8 mg, and 10 mg, for the products prepared in Examples 1, 2 and 3, respectively.

TABLE 2

| | Evaluation of MPM-47 employed as intermediate film Number of Tablets That Showed Visible Browning | | | | | | |
|---|---|---|---|---|---|---|---|
| | Days | | | | | | |
| Sample | 1 | 7 | 14 | 21 | 30 | 45 | 60 |
| Sample I | 80 | 100 | 100 | 100 | 100 | 100 | 100 |
| Sample II | 80 | 100 | 100 | 100 | 100 | 100 | 100 |

Remark:
Sample I was prepared in a manner similar to the manner described in Example 1, and Sample II was prepared in a manner similar to that described in Example 3.

The amounts of the films that were coated on the base tablets (each base tablet weighed 90 mg) were 5 mg and 10 mg, for the samples I and II, respectively.

As is apparent from the results set forth in Table 2 which indicate the effect of MPM-47, the preventive effect on browning cannot be accomplished by simply providing a film of any optionally selected material between the base tablet and the sugar coating layer. As can be seen from the results set forth in Table 1 which indicate the effect of HPC, a significant effect for preventing browning is observed when a water-soluble cellulose ether film is present between the base tablet and the sugar coating layer.

(2) Prevention of delayed disintegration
Samples: Products prepared in Examples 1-3, as set forth hereinafter, which employ hydroxypropyl cellulose (HPC) as the material of the water-soluble cellulose ether film, and a sugar-coated tablet prepared in the same manner as described in Example 1 except that an intermediate film is not provided between the base tablet and the sugar coating layer (control sample).
Test procedure: Each of the invention products and the control sample was examined just after the preparation thereof and again after allowing them to stand at 45° C. for 30 days, with respect to the time (minutes) needed for the complete disintegration thereof according to the disintegration test method described in the Japanese Pharmacopoeia, 9th edition.
Results: As shown in Table 3.

TABLE 3

| | Time needed for the complete disintegration (min.) | |
|---|---|---|
| | Days at 45° C. | |
| Sample | 0 | 30 |
| Product of | 8-10 | 8-11 |

TABLE 3-continued

| | Time needed for the complete disintegration (min.) | |
| --- | --- | --- |
| | Days at 45° C. | |
| Sample | 0 | 30 |
| Example 1 Product of Example 2 | 8–10 | 8–12 |
| Product of Example 3 | 8–10 | 8–12 |
| Control Sample | 6–7 | 17–20 |

The conventional sugar-coated tablet with no intermediate water-soluble cellulose ether film showed an extremely delayed disintegration after it was subjected to the low level heat treatment. In contrast to the above, the products of the present invention, provided with the intermediate film of water-soluble cellulose ether, showed substantially no change of the disintegration time.

The present invention is further described by reference to the following illustrative examples.

EXAMPLE 1

The film-coating solution set forth below was coated on a base tablet (weighing 90 mg) containing 10 mg of Coenzyme $Q_{10}$, in an automatic film coating machine, so that the amount of the film coated on the base tablet was 5 mg.

| Coating solution | |
| --- | --- |
| Hydroxypropyl cellulose | 75 weight parts |
| Polyethylene glycol - 6000 | 25 weight parts |
| Ethanol | 900 weight parts |

The thus-coated tablet was dried by allowing it to stand overnight, and then it was coated with a powder sugar, colored with a syrup containing titanium oxide and finally coated with carnauba wax for glazing, in the conventional manner.

EXAMPLE 2

The procedure described in Example 1 was repeated except that the amount of the film was changed to 8 mg.

EXAMPLE 3

The procedure described in Example 1 was repeated except that the amount of the film was changed to 10 mg.

EXAMPLE 4

The procedure described in Example 1 was repeated except that the material of the film-coating solution had the following composition.

| Coating solution | |
| --- | --- |
| Hydroxypropyl cellulose | 60 weight parts |
| Water | 940 weight parts |

EXAMPLE 5

The procedure described in Example 1 was repeated except that the material of the film-coating solution had the following composition.

| Coating solution | |
| --- | --- |
| Hydroxypropyl cellulose | 50 weight parts |
| Polyethylene glycol - 1500 | 20 weight parts |
| Ethanol | 430 weight parts |
| Water | 500 weight parts |

EXAMPLE 6

The procedure described in Example 1 was repeated except that a base tablet (weighing 90 mg) containing 1 mg of phytonadione (Vitamin $K_1$) was coated.

EXAMPLE 7

The procedure described in Example 1 was repeated except that a base tablet (weighing 90 mg) containing 2 mg of menatetrenone (Vitamin $K_2$) was coated.

EXAMPLE 8

The procedure described in Example 2 was repeated except that a base tablet (weighing 90 mg) containing 15 mg of tocopherol acetate was coated.

The embodiments of the invention in which an exclusive property or privilege is claimed are defined as follows:

1. A sugar-coated tablet, comprising: a core containing low-melting, fat-soluble, active pharmaceutical material; a continuous coating film formed in direct contact with and completely covering said core, said coating film consisting of a material selected from the group consisting of (a) a pharmacologically acceptable water-soluble cellulose ether, (b) a mixture of two or more of said cellulose ethers and (c) a mixture of one or more of said cellulose ethers and a plasticizer therefor, said coating film being free of sugar; and a pharmacologically acceptable, sugar, coating layer over said film, said sugar layer being free of water-soluble cellulose ether, said film being effective to prevent migration of said active pharmaceutical material from said core to said sugar coating layer.

2. A sugar-coated tablet as claimed in claim 1 in which said cellulose ether is selected from the group consisting of methyl cellulose, hydroxypropyl cellulose, hydroxyethyl cellulose, hydroxypropylmethyl cellulose, hydroxyethylmethyl cellulose and mixtures thereof.

3. A sugar-coated tablet as claimed in claim 1 in which said cellulose ether is hydroxypropyl cellulose.

4. A sugar-coated tablet as claimed in claim 1, claim 2 or claim 3, in which the thickness of said coating film is at least 0.02 mm.

5. A sugar-coated tablet as claimed in claim 1, claim 2 or claim 3, in which the thickness of said coating film is from 0.05 to 0.2 mm.

6. A sugar-coated tablet as claimed in claim 1, in which said pharmaceutical material has a melting point of not higher than 70° C.

7. A sugar-coated tablet as claimed in claim 6, in which said pharmaceutical material is Coenzyme Q.

8. A sugar-coated tablet as claimed in claim 1, consisting essentially of said core; said coating film; a layer of powder sugar in direct contact with and covering said coating film; a coloring layer in direct contact with and covering said powder sugar layer; and a wax film in direct contact with and covering said coloring layer.

* * * * *